United States Patent
Jung et al.

(10) Patent No.: US 10,108,385 B2
(45) Date of Patent: Oct. 23, 2018

(54) ELECTRONIC APPARATUS AND DISPLAYING METHOD FOR DISPLAYING DETECTION DATA

(71) Applicant: Samsung Electronics Co., Ltd., Suwon-si, Gyeonggi-do (KR)

(72) Inventors: Jinyung Jung, Seoul (KR); Eunji Ahn, Seoul (KR); Joon Ho Ok, Seoul (KR); Dokshin Lim, Gwacheon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 38 days.

(21) Appl. No.: 15/233,186

(22) Filed: Aug. 10, 2016

(65) Prior Publication Data

US 2017/0046109 A1 Feb. 16, 2017

(30) Foreign Application Priority Data

Aug. 11, 2015 (KR) ........................ 10-2015-0113381

(51) Int. Cl.
| | | |
|---|---|---|
| *G06F 3/14* | (2006.01) | |
| *A61B 5/00* | (2006.01) | |
| *A61B 5/0205* | (2006.01) | |
| *A61B 5/11* | (2006.01) | |
| *G06F 3/0481* | (2013.01) | |
| *G06T 11/60* | (2006.01) | |
| *A61B 5/024* | (2006.01) | |

(Continued)

(52) U.S. Cl.
CPC .............. *G06F 3/14* (2013.01); *A61B 5/0205* (2013.01); *A61B 5/1118* (2013.01); *A61B 5/742* (2013.01); *G06F 3/0481* (2013.01); *G06T 11/60* (2013.01); *A61B 5/0022* (2013.01); *A61B 5/024* (2013.01); *A61B 5/0402* (2013.01); *A61B 5/0816* (2013.01); *A61B 5/4875* (2013.01); *A61B 5/681* (2013.01)

(58) Field of Classification Search
CPC . G06F 3/14; G06F 3/048; G06F 3/015; G06T 11/60; G06T 11/206; A61B 5/681; A61B 5/742
See application file for complete search history.

(56) References Cited

U.S. PATENT DOCUMENTS 5,442,741 A * 8/1995 Hughes ................ G06T 11/206
345/440
8,152,693 B2 4/2012 Nurmela et al.
(Continued)

FOREIGN PATENT DOCUMENTS

JP 2013-200311 A 10/2013
KR 10-2010-00083412 A 7/2010

OTHER PUBLICATIONS

Hodjkins, Kelly, "How to use the Apple Watch to track your activity level", May 12, 2015, http://www.iphonehacks.com/2015/05/how-to-use-apple-watch-to-track-activity-level.html.*

(Continued)

*Primary Examiner* — Michelle L Sams
(74) *Attorney, Agent, or Firm* — Jefferson IP Law, LLP

(57) ABSTRACT

An operating method of an electronic device is provided. The method includes collecting detection data, determining numerical information by analyzing the detection data, and displaying an information display screen comprising at least two display regions identified by a point based on the numerical information.

14 Claims, 11 Drawing Sheets

(51) Int. Cl.
 *A61B 5/0402* (2006.01)
 *A61B 5/08* (2006.01)

(56) References Cited

U.S. PATENT DOCUMENTS

| | | |
|---|---|---|
| 2003/0142135 A1 | 7/2003 | Hori et al. |
| 2005/0131318 A1 | 6/2005 | Peifer et al. |
| 2011/0055741 A1* | 3/2011 | Jeon .................... G06F 3/04817 715/765 |
| 2012/0217801 A1* | 8/2012 | Yamashita ............ H02J 13/001 307/31 |
| 2013/0106684 A1 | 5/2013 | Weast et al. |
| 2013/0197679 A1 | 8/2013 | Balakrishnan et al. |
| 2013/0231575 A1 | 9/2013 | Erkkila et al. |
| 2014/0085077 A1 | 3/2014 | Luna et al. |
| 2014/0200691 A1* | 7/2014 | Lee ........................ A61B 5/1118 700/91 |
| 2015/0022438 A1 | 1/2015 | Hong |
| 2015/0113451 A1* | 4/2015 | Kopp ..................... G06Q 10/00 715/764 |

OTHER PUBLICATIONS

Akanksha, Why Apple Watch Can Be a Treat to Luxury Wrist Watchmakers?, Shopholicx, XP55330708, Retrieved from the Internet: URL:http://shopholicx.com/gadgets/can-apple-watch-change-way-luxury-wrist-watchmakers-make-wear-time-wrist, Nov. 8, 2014.

* cited by examiner

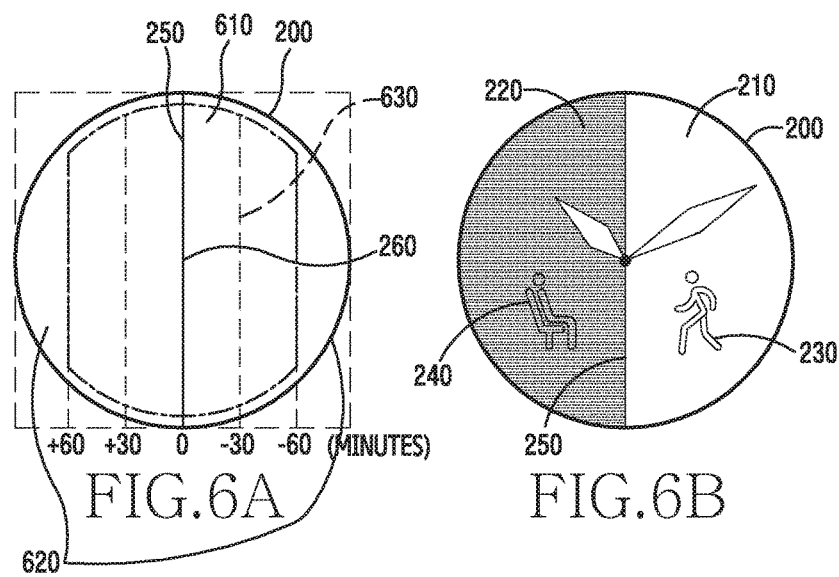
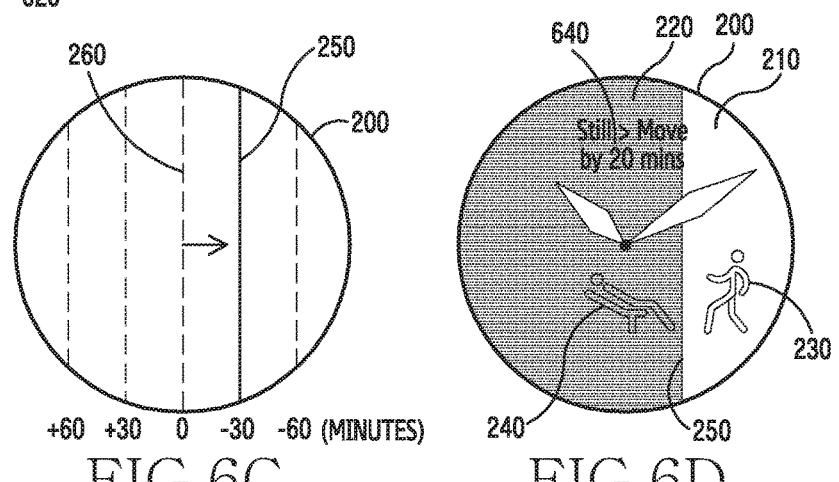
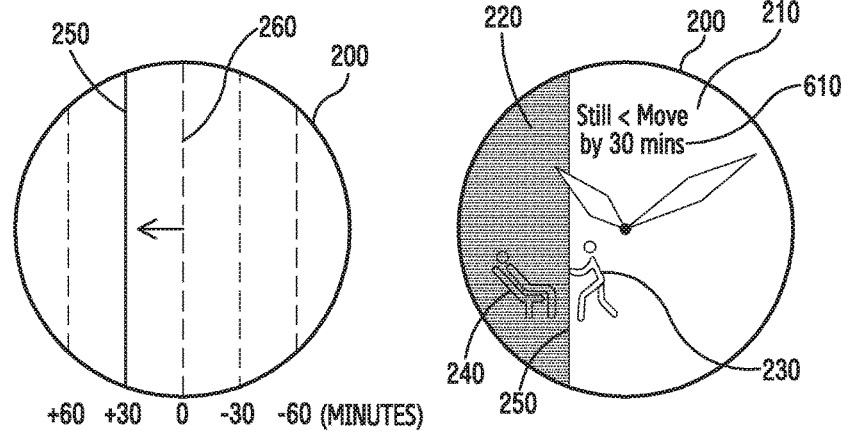
FIG.6A  FIG.6B  FIG.6C  FIG.6D  FIG.6E  FIG.6F

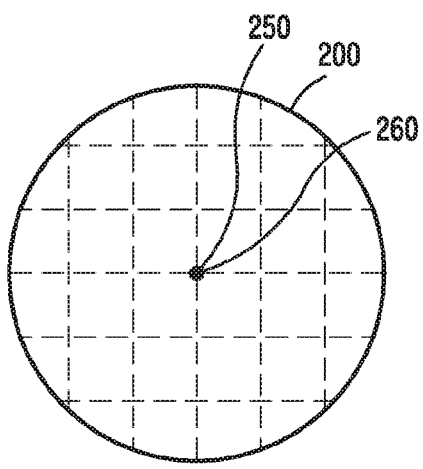
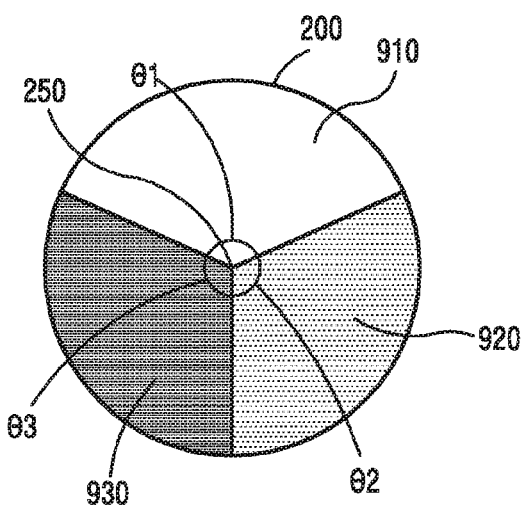
FIG.9A    FIG.9B
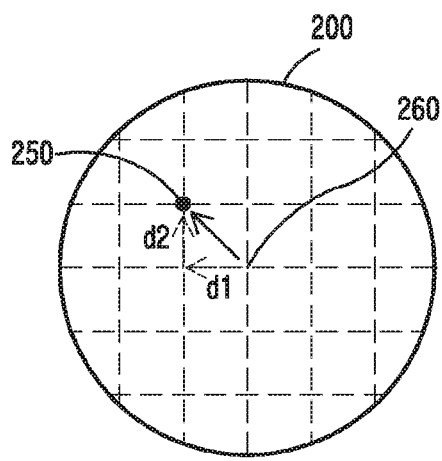
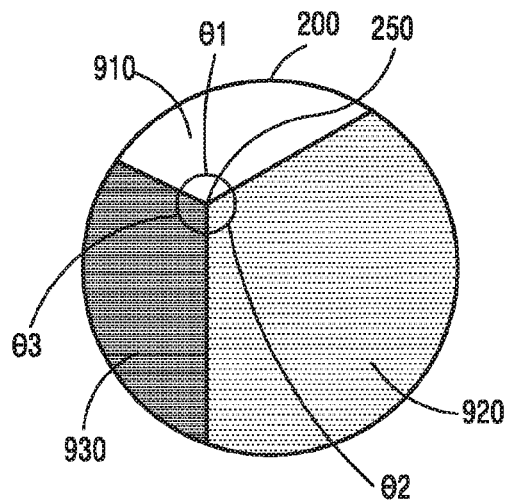
FIG.9C    FIG.9D
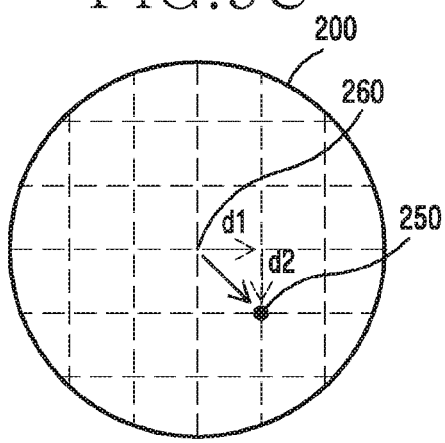
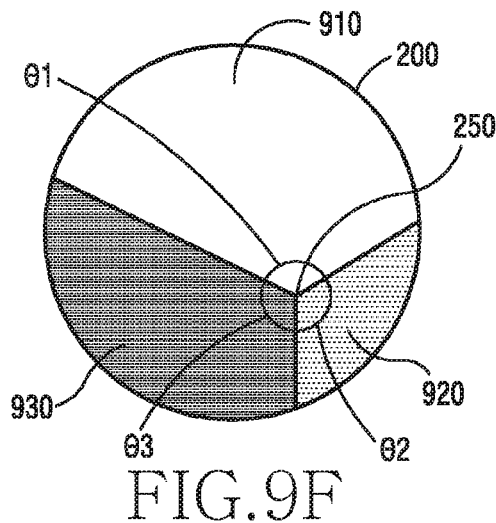
FIG.9E    FIG.9F

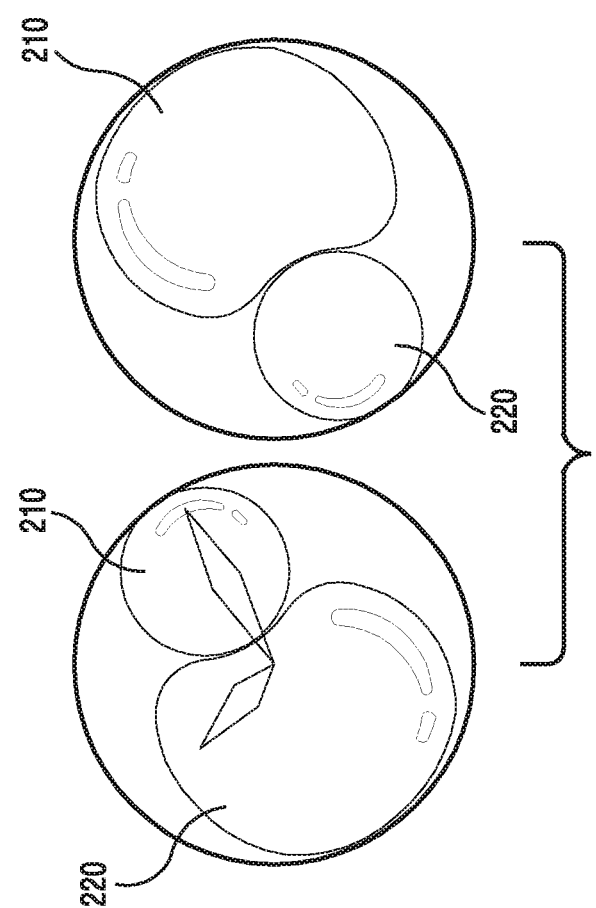
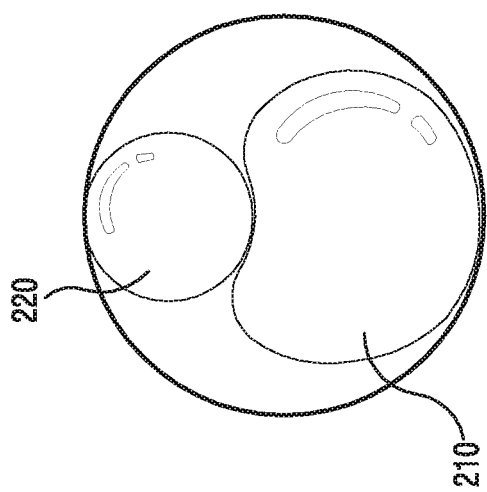
FIG. 11A
FIG. 11B

ELECTRONIC APPARATUS AND DISPLAYING METHOD FOR DISPLAYING DETECTION DATA

CROSS-REFERENCE TO RELATED APPLICATIONS(S)

This application claims the benefit under 35 U.S.C. § 119(a) of a Korean patent application filed on Aug. 11, 2015 in the Korean Intellectual Property Office and assigned Serial number 10-2015-0113381, the entire disclosure of which is hereby incorporated by reference.

TECHNICAL FIELD

The present disclosure relates to an electronic device having a display unit and an operating method thereof.

BACKGROUND

In general, various functions are added to an electronic device to perform a complex function. For example, the electronic device may perform a mobile communication function, a data communication function, an image capturing function, a voice recording function, or the like. Such an electronic device stores and manages a great amount of data. In this case, the electronic device may discover and display data. Herein, the electronic device may have a display unit, and may display data through the display unit.

The above information is presented as background information only to assist with an understanding of the present disclosure. No determination has been made, and no assertion is made, as to whether any of the above might be applicable as prior art with regard to the present disclosure.

SUMMARY

However, the aforementioned electronic device displays information through the display unit in a limited manner. For this reason, there is a problem in that the electronic device cannot provide various interactions. That is, there is a problem in that the electronic device has low usage efficiency and low user convenience.

Aspects of the present disclosure are to address at least the above-mentioned problems and/or disadvantages and to provide at least the advantages described below. Accordingly, an aspect of the present disclosure is to provide an operating method of an electronic device is provided. The operating method of an electronic device includes collecting detection data, determining numerical information by analyzing the detection data, and displaying an information display screen comprising at least two display regions identified by a point based on the numerical information.

In accordance with an aspect of the present disclosure, an electronic device is provided. The electronic device includes a display unit and a controller operatively coupled to the display unit, wherein the controller is configured to collect detection data, determine numerical information by analyzing the detection data and display an information display screen comprising at least two display regions identified by a point based on the numerical information.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIGS. 6A to 6F, FIGS. 7A to 7F, FIGS. 8A to 8F, FIGS. 9A to 9F, FIGS. 10A and 10B, and FIGS. 11A and 11B illustrate examples of a method of displaying an information display screen according to embodiments of the present disclosure.

Throughout the drawings, it should be noted that like reference numbers are used to depict the same or similar elements, features, and structures.

DETAILED DESCRIPTION

Figure 1:
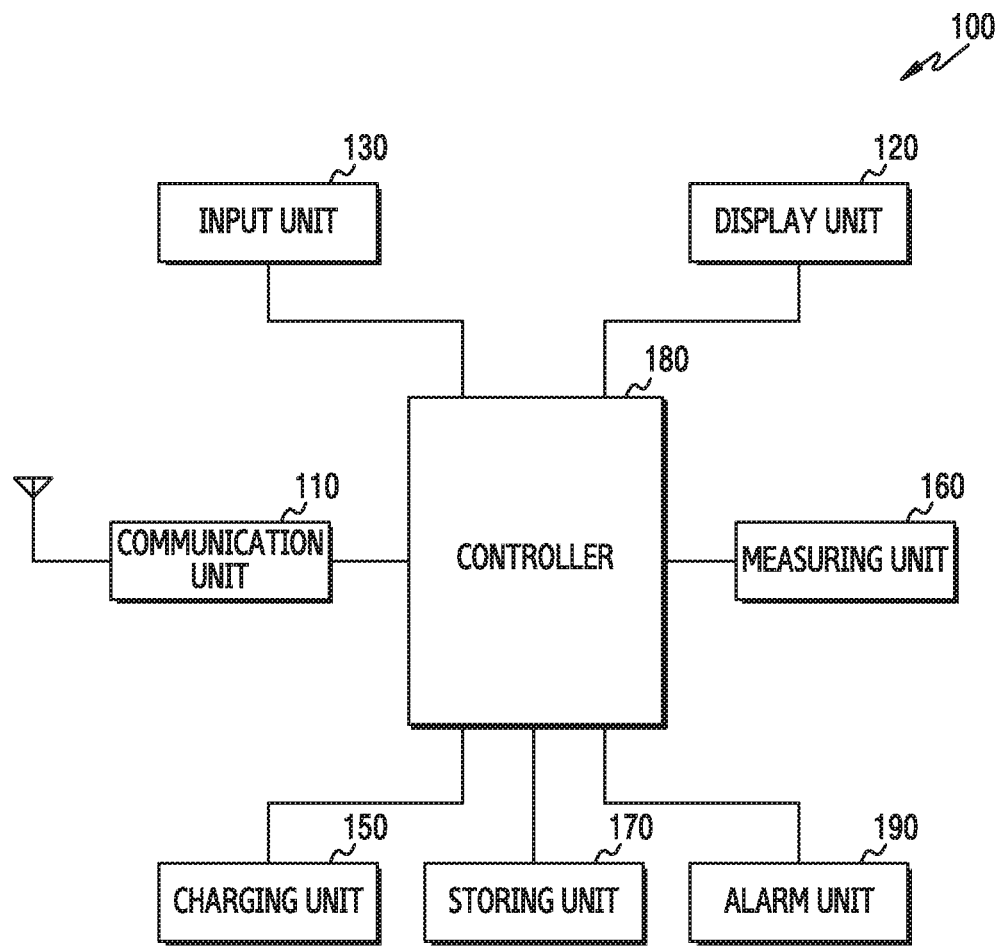
FIG. 1 is a block diagram illustrating an electronic device according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the following description, the term "detection data" implies data detected in an electronic device when the electronic device performs various functions. The detection data may be generated in various manners. The detection data may be generated in accordance with communication between the electronic device and an external device. For example, the detection data may include at least any one of a call, a short message, a multimedia message, a social network service (SNS) message, and an instant message. Alternatively, the detection data may be measured in the electronic device. For example, the detection data may include activity data and biometry data. The activity data may include at least any one of a motion, an inactivity, a light active (or a light walking), and a healthy pace. In addition, the biometry data may include at least any one of a blood sugar, a heart rate (or a heartbeat), an electrocardiogram, a sweat, a blood pressure, a nutrition, a sleep, a respiratory rate, an oxygen saturation, a water intake, and a caffeine intake. Alternatively, the detection data may be generated in accordance with a user input of the electronic device. For example, the detection data may include at least any one of a schedule and memo based on the user input.

An electronic device and an operating method according to an embodiment of the present disclosure can display detection data that can be detected on a real-time basis by converting the data to numerical information, and thus can intuitively show a competitive or balanced state between comparable pieces of information. That is, the numerical information can be shown through visualization by using display regions of an information display screen.

In addition, the electronic device and the operating method according to an embodiment of the present disclosure may motivate a user who has recognized the competitive or balanced state between the pieces of information to perform an operation for updating the information to a more preferable state.

In addition, the electronic device and the operating method according to an embodiment of the present disclosure can change the information display screen by detecting an input of various actions such as tapping or shaking of a device, or can provide a reaction depending on a property of matter. A user experience can be extended by providing such an amusing experience.

FIG. 1 is a block diagram illustrating an electronic device according to an embodiment of the present disclosure.

Figure 2:
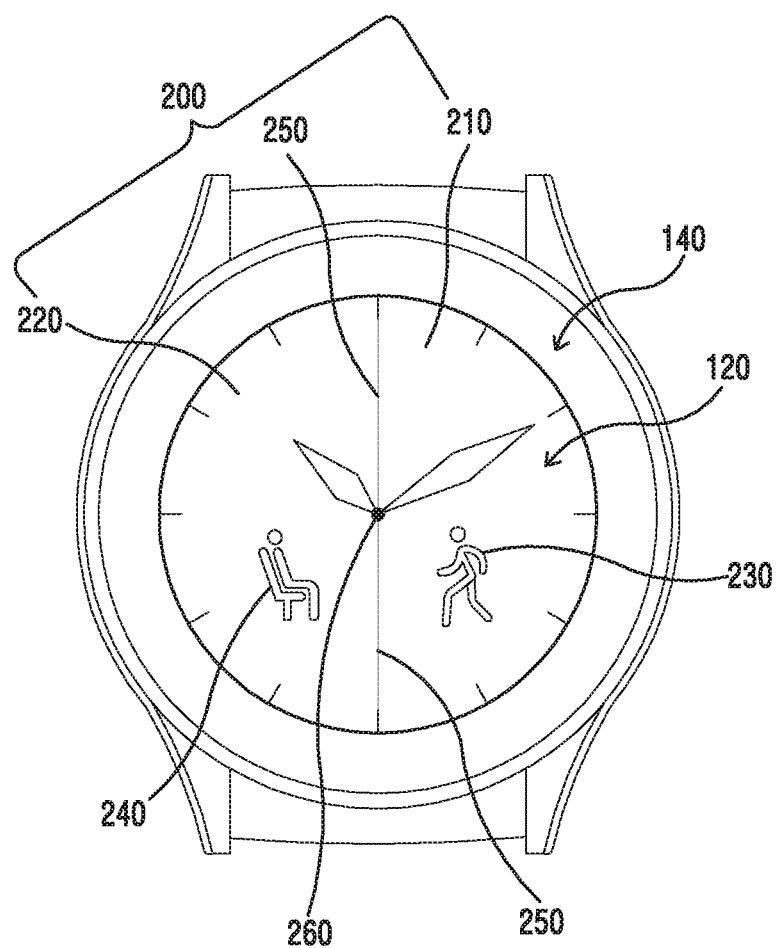
FIGS. 2 and 3 illustrate an example of implementing an electronic device according to embodiments of the present disclosure.

FIG. 2 and illustrates an example of implementing an electronic device according to an embodiment of the present disclosure. FIG. 2 illustrates a case where the electronic device according to the various embodiments is a watch-type wearable device.

Figure 3:
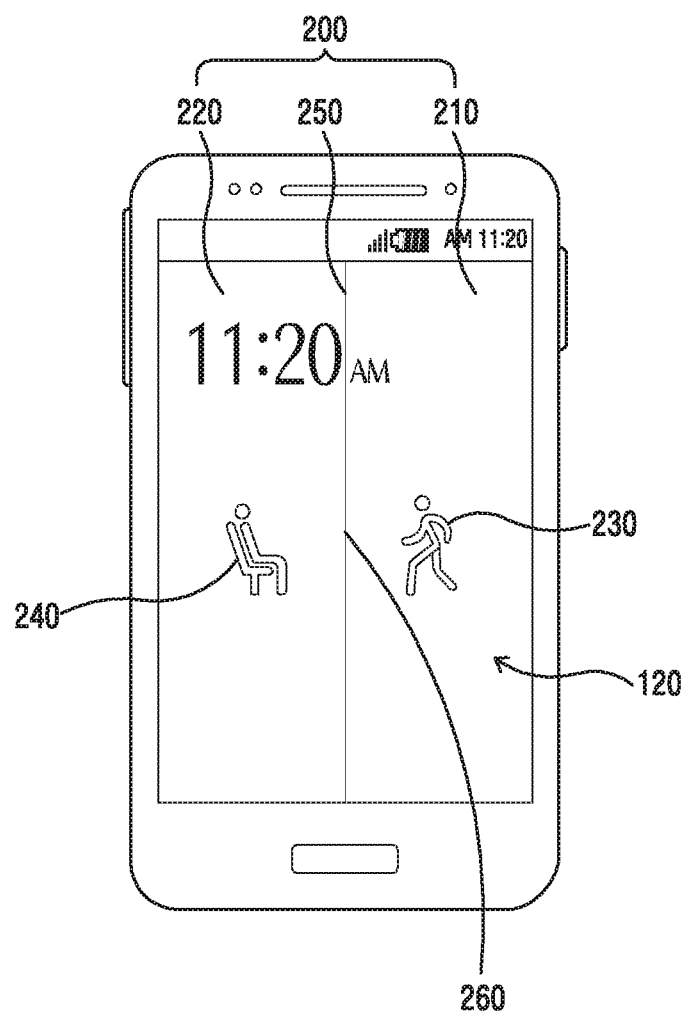

FIG. 3 illustrates a case where the electronic device according to various embodiments is a display device such as a portable terminal or the like according to an embodiment of the present disclosure.

Referring to FIG. 1, an electronic device 100 according to various embodiments may include a communication unit 110, a display unit 120, an input unit 130, a charging unit 150, a measuring unit 160, a storing unit 170, a controller 180, and an alarm unit 190.

The communication unit 110 performs communication in the electronic device 100. In this case, the communication unit 110 may communicate with an external device (not shown) by using various communication schemes. Herein, the communication unit 110 may perform at least any one of wireless communication and wired communication. For this, the communication unit 110 may access at least any one of a mobile communication network and a data communication network. Alternatively, the communication unit 110 may perform near range communication. For example, the external electronic device may include an electronic device, a base station, a server, and a satellite. In addition, the communication scheme may include long term evolution (LTE), wideband code division multiple access (WDCMA), global system for mobile communications (GSM), wireless fidelity (WiFi), Bluetooth, and near field communications (NFC).

The display unit 120 outputs display data in the electronic device 100. The display unit 120 may include a liquid crystal display (LCD), a light emitting diode (LED) display, an organic light-emitting diode (OLED) display, a micro electro mechanical system (MEMS) display, and an electronic paper display. In this case, the display unit 120 may be implemented in various shapes. Herein, the display unit 120 may be implemented in a shape of a circle as shown in FIG. 2. Meanwhile, the display unit 120 may be implemented in a shape of a polygon, for example, a quadrangle, as shown in FIG. 3.

The input unit 130 generates input data in the electronic device 100. In this case, the input unit 130 may generate the input data in accordance with a user input of the electronic device 100. In addition, the input unit 120 may include at least one input means. The input unit 130 may include a key pad, a dome switch, a physical button, a touch panel, a jog & shuttle, and a sensor. In this case, the input unit 130 may be implemented as a touch screen by being coupled with the display unit 120.

Meanwhile, if the electronic device 100 is the wearable device of FIG. 2, the input unit 130 may include a rotation unit 140. The rotation unit 140 may generate rotation input data in the electronic device 100. In this case, the rotation unit 140 may generate the rotation input data in accordance with the user input. In addition, the rotation unit 140 may be engaged with an edge of the display unit 120 in a rotatable manner. In this case, the rotation unit 140 may be implemented in various shapes. Herein, the rotation unit 140 may be implemented in a shape of a ring. For example, the rotation unit 140 may be implemented in a shape of a circular ring. That is, the rotation unit 140 may encompass the display unit 120. Further, the rotation unit 140 may rotate in a clockwise direction or a counter-clockwise direction about a central axis of the display unit 120. Alternatively, although not shown, the rotation unit 140 may be implemented in a shape of a cylinder. For example, the rotation unit 140 may be implemented in a shape of a crown of an analog watch. That is, at least one portion of the rotation unit 140 may be inserted internally to the electronic device 100, and the remaining portions of the rotation unit 140 may protrude externally from the electronic device 100. Further, the rotation unit 140 may rotate in a clockwise direction or a counter-clockwise direction about a vertical axis orthogonal to the central axis of the display unit 120. In addition thereto, the rotation unit 140 may generate squeezing (or pressing) input data. In this case, the rotation unit 140 may generate the squeezing (or pressing) input data in accordance with the user input.

The charging unit 150 supplies power in the electronic device 100. In this case, the charging unit 150 may be charged by receiving power from an external power source (not shown). Herein, the charging unit 150 may receive power by being connected to the external power source in a wired manner. Alternatively, the charging unit 150 may receive power by being connected to the external power source in a wireless manner. In addition, the charging unit 150 may convert and store the power. Further, the charging unit 150 may supply the power to constitutional elements of the electronic device 100. The charging unit 150 may be disposed to face a rear side of the display unit 120.

The measuring unit 160 measures detection data in the electronic device 100. In this case, the measuring unit 160 may detect the detection data from a surrounding environment of the electronic device 100. Herein, the detection data may include activity data and biometry data. For example, the activity data may include at least any one of a motion, an inactivity, a light active (or a light walking), and a healthy pace. Further, the biometry data may include at least any one of a heart rate (or a heartbeat), an electrocardiogram, a respiratory rate, a water intake, and a caffeine intake. The measuring unit 160 may include a variety of sensors. For example, the measuring unit 160 may include a pedometer sensor.

The storing unit 170 may store operating programs of the electronic device 100. In this case, the storing unit 170 may store a plurality of functions. For example, the function may be an application. Herein, the functions may include a measurement function and an event management function. In addition, the storing unit 170 may store a program for displaying and controlling an information display screen. Further, the storing unit 170 stores data which is generated while executing programs. In this case, the storing unit 170 may store detection data.

The controller 180 controls an overall operation in the electronic device 100. The controller 180 may perform a plurality of functions. Herein, the controller 180 may include a function processor for each function. The function processor may process each function in practice. For example, the function processor may be an application processor (AP).

In this case, the controller 180 may collect the detection data. The controller 180 may collect the detection data via the measuring unit 160. The controller 180 may collect the detection data via the communication unit 110. The controller 180 may collect the detection data via the storing unit 170. The controller 180 may analyze the detection data and may determine numerical information. In addition, the controller 180 may generate an information display screen 200 in accordance with the numerical information. Further, the controller 180 may display the information display screen 200.

Herein, the controller 180 may output the information display screen 200 via the display unit 120 in a shape of a circle as shown in FIG. 2. Alternatively, the controller 180 may output the information display screen 200 via the display unit 120 in a shape of a polygon, for example, a quadrangle, as shown in FIG. 3. The controller 180 may display the information display screen 200 as a background screen, and may display it as a function execution screen. If the information display screen 200 is displayed as the background screen, a watch may be displayed together. In addition, the information display screen 200 may include at least two display regions 210 and 220 and a point 250.

The display regions 210 and 220 may be determined in accordance with the numerical information. An attribute (e.g., the number, an area, a length, a volume, or a size) of the display regions 210 and 220 may be determined on the basis of the numerical information. Superiority and inferiority between pieces of numerical information may be expressed by using the display regions 210 and 220. The controller 180 may intuitively show a competitive or balanced state between pieces of comparable numerical information by using the display regions 210 and 220. The controller 180 may show the numerical information through visualization by using the display regions 210 and 220. Therefore, the information display screen 200 may be used to motivate a user who has recognized the competitive or balanced state between the pieces of numerical information to perform an operation for updating the information to a more preferred state.

Herein, the display regions 210 and 220 may include various shapes. For example, the shape of the display regions 210 and 220 may include a shape of a semi-circle, a shape of a circle, a shape of a block, a shape of a line, or the like. The display regions 210 and 220 may include contrasting shapes to compare respective pieces of numerical information.

Meanwhile, the display regions 210 and 220 may include various colors. The color may be determined such that the display regions 210 and 220 can be contrasted with each other. The display regions 210 and 220 may include different colors.

The controller 180 may display a plurality of display regions according to the number of pieces of detection data to be displayed. For example, if there are two pieces of detection data to be displayed, i.e., a heart rate of a user and a heart rate of an opposite party, the display regions 210 and 220 may include the first display region 210 and the second display region 220. The controller 180 may display the first display region 210 as the heart rate of the user, and may display the second display region 220 as the heart rate of the opposite party. Meanwhile, the controller 180 may display a plurality of display regions according to the number of pieces of numerical information identified from one piece of detection data. For example, if the detection data is data detected from a pedometer and if there are two pieces of information to be displayed, i.e., an active time and an inactivity time, as numerical information identified from this, the display regions 210 and 220 may include the first display region 210 and the second display region 220. The controller 180 may display the first display region 210 as the active time, and may display the second display region 220 as the inactivity time.

The display regions 210 and 220 may include objects 230 and 240. The objects 230 and 240 may include a background image, an item, and an icon which represent the numerical information displayed in the display regions 210 and 220. A structure, position, size, shape, or the like of the objects 230 and 240 may be determined according to the numerical information displayed in each of the display regions 210 and 220. The objects 230 and 240 may be displayed variously to express superiority and inferiority between pieces of information of the display regions 210 and 220. For example, the object 230 of the first display region 210 for displaying superior information may include a shape of pushing the second display region 220 for displaying inferior information. Alternatively, the object 230 of the first display region 210 for displaying the superior information may include a shape of pulling the second display region 220 for displaying the inferior information. Alternatively, the objects 230 and 240 may be displayed such that a size can be compared between pieces of information by including a shape of measuring a weight of the display regions 210 and 220, for example, a shape of a scale.

The point 250 may be located in an edge of the display regions 210 and 220. Accordingly, the point 250 may identify or divide the display regions 210 and 220. The point 250 may move from a center 260 of the information display screen 200 in accordance with numerical information. According to the movement of the point 250, an attribute (e.g., an area, a length, a volume, a position, or a size) of the display regions 210 and 220 may be determined. The point 250 may be any one of a dot, a line, and a plane.

The alarm unit 190 generates an alarm signal in the electronic device 100. Herein, the alarm signal may include at least any one of a light-emitting signal, an audio signal, and a vibration signal.

Figure 4:
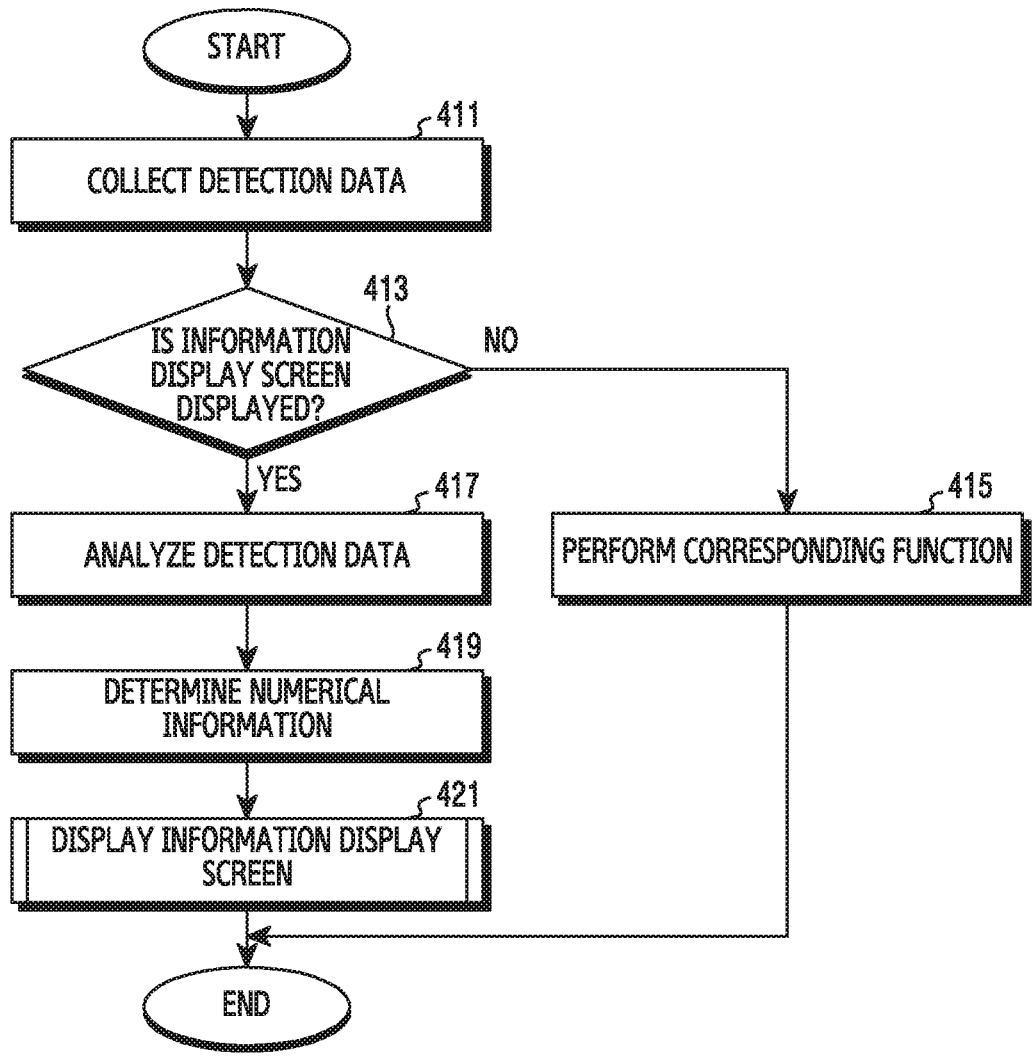
FIG. 4 is a flowchart illustrating a procedure of performing an operating method of an electronic device according to an embodiment of the present disclosure.

FIG. 4 is a flowchart illustrating a procedure of performing an operating method of an electronic device according an embodiment of the present disclosure.

Referring to FIG. 4, an operating method of the electronic device 100 according to an embodiment of the present disclosure begins with collecting of detection data by the controller 180 in operation 411. In this case, the controller 180 may collect the detection data from a surrounding environment of the electronic device 100 via the measuring unit 160. For this, the controller 180 may activate at least any one of sensors of the measuring unit 160. Herein, the controller 180 may collect the detection data via the measuring unit 160. In this case, the detection data may be activity data. For example, the activity data may include at least any one of a motion, an inactivity, a light walking, and a healthy pace. Alternatively, the controller 180 may collect biometry data via the measuring unit 160. For example, the biometry data may include at least any one of a heart rate, a sleep, a water intake, and a caffeine intake. Further, the controller 180 may collect the detection data through communication with an external device via the communication unit 110. Herein, the controller 180 may collect detection data including a call, a short message, a multimedia message, or an instant message via the communication unit 110. Further, the controller 180 may collect detection data stored in the storing unit 170 through a user input. Herein, the controller 180 may collect detection data including a memo or a schedule via the storing unit 170.

The detection data may be collected during the electronic device 100 is worn. In this case, the controller 180 may collect the detection data via the measuring unit 160. That is, when the electronic device 100 is worn, this may be detected as a request for executing a function of collecting the detection data by the controller 180. For this, the measuring unit 160 may include an accelerometer. In addition, the controller 180 may detect the wearing of the electronic device 100 via the accelerometer. For example, upon detection of a movement of the electronic device 100 via the accelerometer, the controller 180 may determine whether charging is performed in the charging unit 150. Herein, if it is determined that the charging is not performed in the charging unit 150, the controller 180 may determine that the electronic device 100 is worn. Alternatively, if the charging is performed in the charging unit 150, the controller 180 may determine that the electronic device 100 is not worn.

Meanwhile, even if the electronic device 100 is not worn, the controller 180 may frequently collect the detection data. In this case, the controller 180 may collect the detection data via the communication unit 110. Alternatively, the controller 180 may collect the detection data in accordance with the user input via the storing unit 170.

Next, the controller 180 detects a request for displaying the information display screen 200 in operation 413. For example, the information display screen 200 may be a background screen. In this case, the request for displaying the information display screen 200 may be a request for transitioning the display unit 120 from an off state to an on state. Further, the request for displaying the information display screen 200 may be a request for ending a function execution screen currently being displayed. Furthermore, the request for displaying the information display screen 200 may be a request for displaying the information display screen 20 in a foreground.

Meanwhile, if the request for displaying the information display screen 20 is not detected in operation 413, the controller 180 may perform a corresponding function in operation 415. That is, the corresponding function may include an operation of displaying a different screen other than the information display screen 200. Further, the corresponding function may include a setup function for the information display screen 200, for example, an initial setup or setup change function. That is, the corresponding function may include an operation of selecting numerical information or detection data to be displayed in the information display screen 200, or selecting an attribute (e.g., the number, a shape, or a color) of the display regions 201 and 220, or selecting the objects 210 and 220, or setting a detection time of the detection data.

Next, if the request for displaying the information display screen 200 is detected in operation 413, the controller 180 may analyze the detection data in operation 417. For example, if the detection data is activity data, an active time of the measuring unit 160 may be analyzed. Alternatively, the number of times of performing detection by the measuring unit 160 may be analyzed and then may be converted into time. Meanwhile, the controller 180 may analyze the detection data within a specific time. The controller 180 may analyze the detection data between a point of receiving the request for displaying the information display screen 200 and a basic point. For example, the controller 180 may analyze the detection data up until one hour ago from the point of receiving the request for displaying the information display screen 200. The basic point may be separately set or may be randomly determined.

Next, the controller 180 may determine numerical information on the basis of the analyzed detection data in operation 419. The numerical information is information to be displayed in the information display screen 200. The numerical information may include positive information and negative information. The positive information and the negative information may be a pair of information that can be compared or contrasted with each other. For example, the positive information may be an active time, and the negative information may be an inactive time (or an inactivity time). Further, the positive information may be the number of read mails, and the negative information may be the number of unread mails. Furthermore, the positive information may be a heart rate of a user, and the negative information may be a heart rate of an opposite party.

Next, in operation 421, the controller 180 may display the information display screen 200 via the display unit 120. Alternatively, the previously displayed information display screen 200 may be displayed again dimly. In this case, when the detection data is data that can be detected upon wearing of the electronic device 100 and when there is a request for displaying the information display screen 200, this may be a case where the controller 180 determines that the electronic device 100 is not worn.

Figure 5:
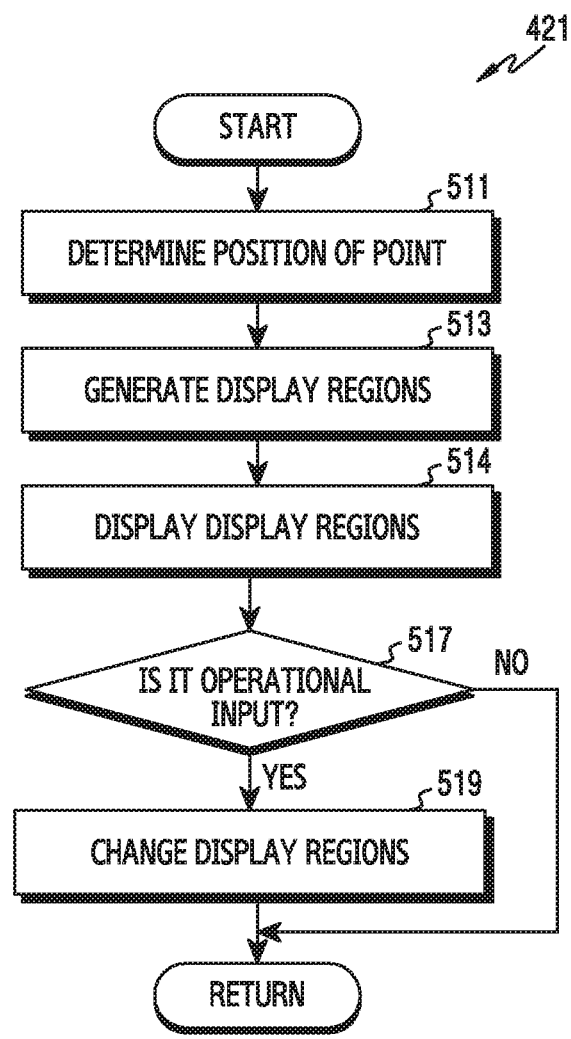
FIG. 5 is a flowchart illustrating a procedure of performing an operation of displaying an information display screen of FIG. 4 according to an embodiment of the present disclosure.

FIG. 5 is a flowchart illustrating a procedure of performing an operation of displaying the information display screen 200 of FIG. 4 according to an embodiment of the present disclosure.

FIGS. 6A to 6F, FIGS. 7A to 7F, FIGS. 8A to 8F, FIGS. 9A to 9F, FIGS. 10A and 10B, and FIGS. 11A and 11B illustrate examples for describing a method of displaying an information display screen according to various embodiments of the present disclosure.

Referring to FIGS. 6A to 6F, FIGS. 7A to 7F, FIGS. 8A to 8F, FIGS. 9A to 9F, FIGS. 10A and 10B, and FIGS. 11A and 11B, it is described a case where detection data is a motion detected by a pedometer, positive information is an active time, and negative information is an inactivity time.

As shown in FIG. 5, the controller 180 may determine a position of the point 250 in operation 511. The position of the point 250 may be determined according to a difference value between the positive information and the negative information. That is, the controller 180 may determine the difference value between the positive information and the negative information, and may determine a distance from the center 260 of the information display screen 200 according to the difference value. The controller 180 may move the point 250 according to the distance from the center 260 of the information display screen 200. The point 250 may have a shape of a line as shown in FIGS. 6A to 6F, or may have a shape of a dot as shown in FIGS. 7A to 7F.

Next, the controller 180 may generate the display regions 210 and 220 according to the movement of the point 250 in operation 513. The controller 180 may generate the display regions 210 and 220 on the basis of the point 250. Next, the controller 180 may display the display regions 210 and 220 via the display unit 120 in operation 514.

Referring to FIG. 6A, the information display screen 200 may include a point moving region 610 and an object ensuring region 620.

The point moving region 610 is a region in which the point 250 can move. Unit axes 630 may be defined in the point moving region 610. The unit axes 630 may identify the point moving region 610 according to a size of numerical information. Alternatively, the unit axes 630 may constantly identify a difference value between positive information and negative information. For example, the unit axes 630 may identify the difference value between the positive information and the negative value in unit of 30 minutes. Therefore, the unit axes 630 may guide the difference value between the positive information and the negative information as +60, +30, 0, −30, and −60 minutes. The point 250 may move from the center 260 of the information display screen 200 according to the difference value on the basis of the unit axes 630.

Meanwhile, the controller 180 may not output the unit axes 630 to the display unit 120. Alternatively, the controller 180 may output the unit axes 630 to the display unit 120. Therefore, advantageously, a user of the electronic device 100 can intuitively know numerical information of the positive information and the negative information.

The object ensuring region 620 may be disposed to an outer portion of the point moving region 610. For example, the object ensuring region 620 may be disposed to a lateral side of the point moving region 610. The object ensuring region 620 is a region in which the point 250 cannot move. Therefore, the unit axes 630 may not be defined in the object ensuring region 620. The object ensuring region 620 may allow the objects 230 and 240 to be displayed by ensuring the display regions 210 and 220 to have a minimum size.

Meanwhile, the point 250 may have a shape of a line, and in an initial state, the point 250 is located at the center 250 of the information display screen 200. Therefore, in the initial state, the information display screen 200 may be displayed as shown in FIG. 6B. Alternatively, it may also be displayed in the same manner even if the positive information and the negative information are identical and thus the difference value thereof is 0. Meanwhile, the first display region 210 and the second display region 220 may be displayed in a shape of a semi-circle. The first display region 210 and the second display region 220 may be displayed by including the objects 230 and 240 respectively representing the display region 210 and the display region 220. The first display region 210 may be displayed in blue color, and the second display region 220 may be displayed in grey color.

Meanwhile, upon detecting the request for displaying the information display screen 200, the position of the point 250 may be determined in operation 511. The point 250 may move from the center 250 of the information display screen 200. The point 250 may move by a distance corresponding to the difference value between the positive information and the negative information. For example, as shown in FIG. 6C, when numerical information determined from detection data has positive information indicating 10 minutes and negative information indicating 40 minutes, a difference value between the positive information and the negative information is −30 minutes. Therefore, the point 250 may move by a distance corresponding to −30 minutes from the center 260.

Referring to FIG. 6D, the first display region 210 and the second display region 220 may be displayed according to the movement of the point 250 in FIG. 6C. The first display region 210 may be decreased, and the second display region 220 may be increased. That is, the first display region 210 may be displayed in a smaller size than the second display region 220. In this case, if a numeric value of the negative information is greater than that of the positive information, it may be displayed such that the second display region 220 for displaying the negative information pushes the first display region 210 for displaying the positive information. For example, it may be an image which shows that the object 240 of the second display region 220 pushes the point 250. Further, it may be an image which shows that the object 230 of the first display region 210 is pushed by the object 240.

Meanwhile, the controller 180 may further display a text 640 capable of comparing pieces of numerical information of the display regions 210 and 220. Regarding the text 640, a comparison result and a correct numeric value for information visualized as the first display region 210 and the second display region 220 may be provided explicitly as the text 640. The controller 180 may display or omit the text 640.

Referring to FIG. 6E, when numerical information determined from detection data has positive information indicating 40 minutes and negative information indicating 10 minutes, a difference value between the positive information and the negative information is +30 minutes. Therefore, the point 250 may move by a distance corresponding to +30 minutes from the center 260.

Referring to FIG. 6F, according to the movement of the point 250 in FIG. 6E, the first point region 210 for displaying positive information may be displayed to a right side of the point 250, and the second display region 220 for displaying negative information may be displayed to a left side of the point 250. Therefore, the first display region 210 may be displayed in a greater size than the second display region 220. In this case, if a numeric value of the positive information is greater than that of the negative information, it may be displayed such that the first display region 210 for displaying the positive information pushes the second display region 220 for displaying the negative information. For example, it may be an image which shows that the object 230 of the first display region 210 pushes the point 250.

Referring to FIGS. 7A to 7F, in the information display screen 200 according to various embodiments, the point 250 may have a shape of a dot, and the first display region 210 and the second display region 220 may have a shape of a circle.

Figure 7A:
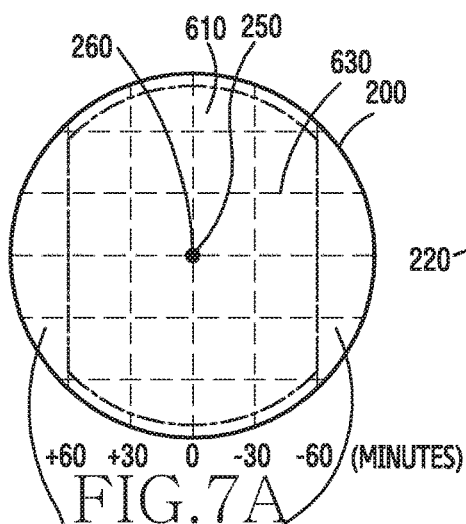

As shown in FIG. 7A, the information display screen 200 may include the point moving region 610 and the object ensuring region 620. The unit axes 630 may be defined in the point moving region 610. The unit axes 630 may identify the point moving region 610 according to a size of numerical information. Alternatively, the unit axes 630 may constantly identify a difference value between positive information and negative information. For example, the unit axes 630 may be formed of an x-axis and a y-axis according to the difference value between the positive information and the negative information. In this case, the point 250 may move the unit axis 630 of any one of the x-axis and the y-axis. Alternatively, the point 250 may move the unit axis 630 of both of the x-axis and the y-axis.

The object ensuring region 620 may be disposed to an outer portion of the point moving region 610. Therefore, the unit axes 630 may not be defined in the object ensuring region 620. The object ensuring region 620 may allow the objects 230 and 240 to be displayed by ensuring the display regions 210 and 220 to have a minimum size.

Figure 7B:
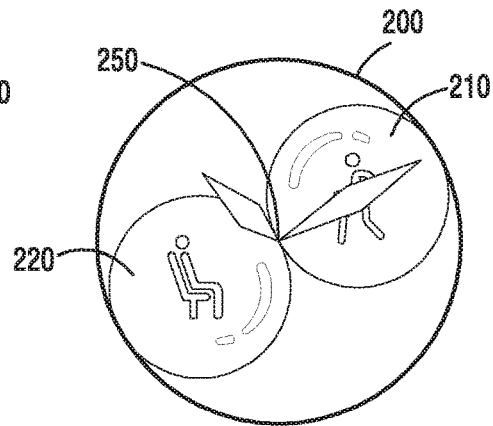

As shown in FIG. 7A, in an initial state, the point 250 is located at the center 250 of the information display screen 200. Therefore, in the initial state, the information display screen 200 may be displayed such that the first display region 210 and the second display region 220 have the same size as shown in FIG. 7B. Alternatively, it may also be displayed in the same manner even if the positive information and the negative information are identical and thus the difference value thereof is 0.

Figure 7C:
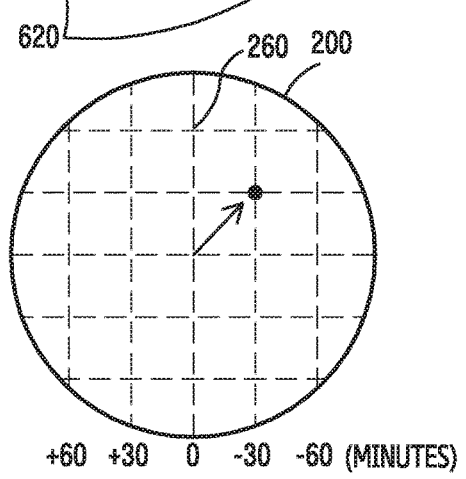
Figure 7D:
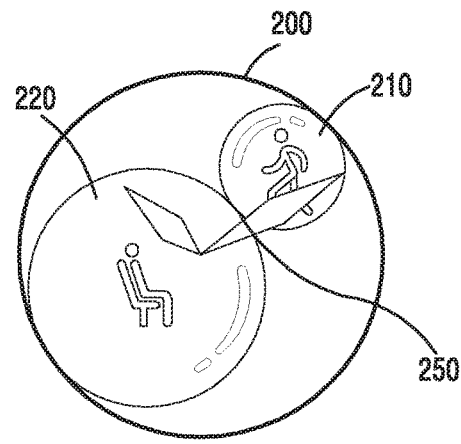

Referring to FIG. 7C, if a numerical difference value between positive information and negative information is −30, the point 250 may move by a distance corresponding to −30. In this case, the point 250 may move the unit axis 630 of both of the x-axis and the y-axis. Referring to FIG. 7D, according to the movement of the point 250, the first display region 210 may be displayed by being generated as a circle smaller in size than the second display region 220.

Figure 7E:
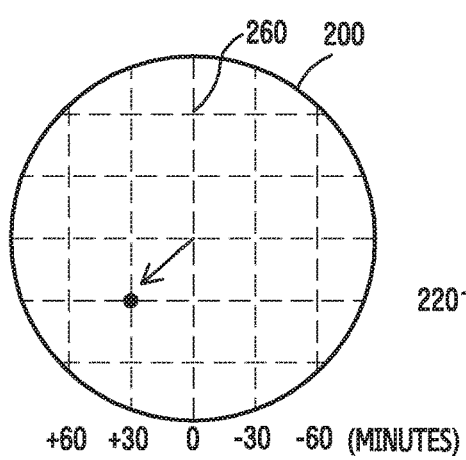
Figure 7F:
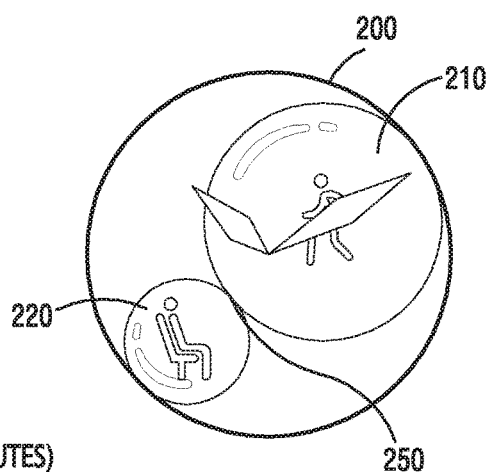

Referring to FIG. 7E, if a numerical difference value between positive information and negative information is +30, the point 250 may move by a distance corresponding to +30. In this case, the point 250 may move the unit axis 630 of both of the x-axis and the y-axis. According to the movement of the point 250, the first display region 210 may be displayed by being generated as a circle greater in size than the second display region 220.

Referring to FIGS. 8A to 8F, the information display screen 200 according to various embodiments may include three display regions 810, 820, and 830 if there are three pieces of information to be displayed, i.e., a light walking time, a healthy pace time, and an inactivity time, as information identified from data sensed from a pedometer. That is, the information display screen 200 may include the point 250, the first display region 810, the second display region 820, and the third display region 830. Herein, the positive information may be the light walking time and the healthy pace time, and the negative information may be the inactivity time. The positive information may include first positive information and second positive information, and the first positive information may be the light walking time, and the second positive information may be the healthy pace time. The first display region 810 may display the light walking time as the first positive information. The second display region 820 may display the healthy pace time as the second positive information. The third display region 830 may display the inactivity time as negative information. The point 250 may move from the center 260 in accordance with a first difference value which is a numerical difference between the positive information and the negative information. Further, the point 250 may move from the center 260 in accordance with a second difference value which is a numerical difference between the first positive information and the second positive information. That is, the point 250 may move from the center 260 by considering both of the first difference value and the second difference value.

Figure 8A:
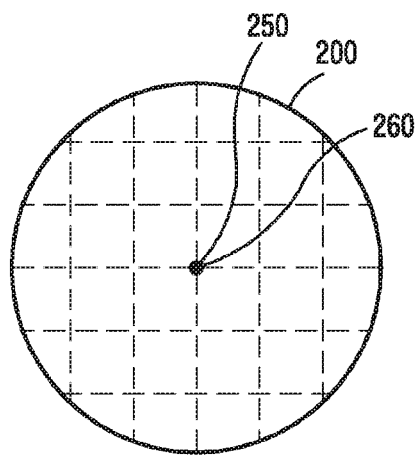
Figure 8B:
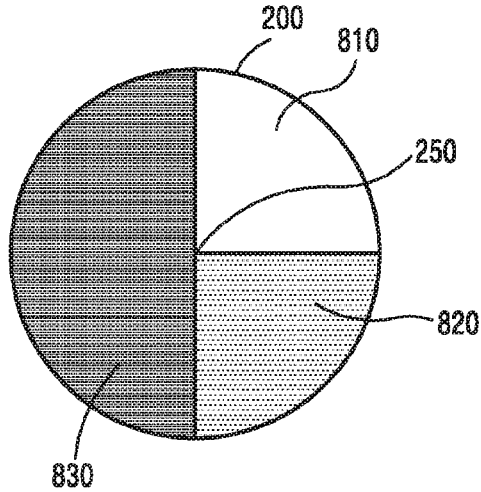

Referring to FIG. 8A, in an initial state, the point 250 may be located in the center 260 of the information display screen 200, and as shown in FIG. 8B, the display regions 810, 820, and 830 may be displayed.

Figure 8C:
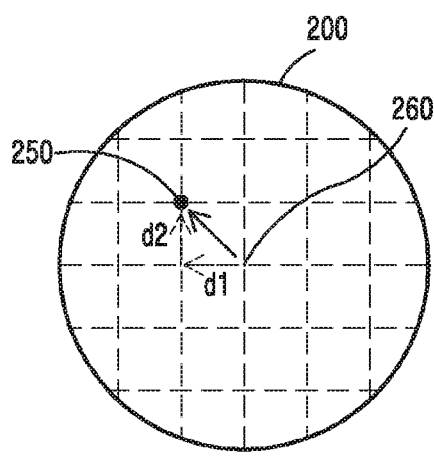
Figure 8D:
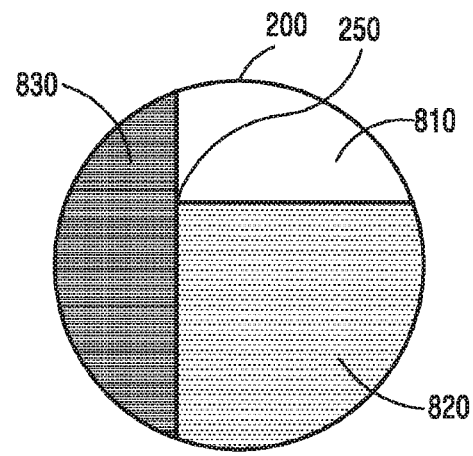

Referring to FIG. 8C, if positive information is superior to negative information in regard to numerical information determined from detection data and if second positive information is superior to first positive information in regard to the positive information, the point 250 may move from the center 260. That is, the point 250 may move from the center 260 by a first distance d1 according to a first difference value between the positive information and the negative information, and thereafter may move from the center 260 by a second distance d2 according to a second difference value between the first positive information and the second positive information. Next, as shown in FIG. 8D, the display regions 810, 820, and 830 may be displayed by being generated in different sizes according to the movement of the point 250.

Figure 8E:
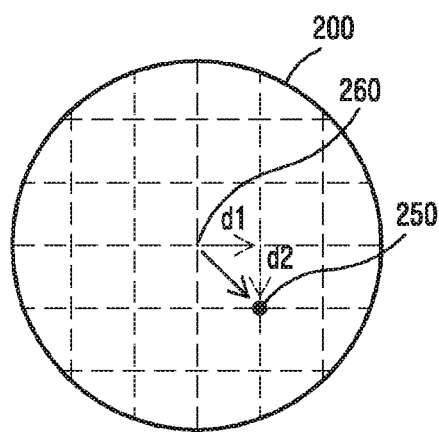
Figure 8F:
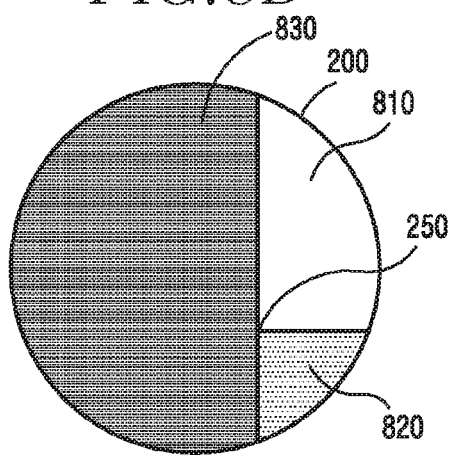

Referring to FIG. 8E, if negative information is superior to positive information in regard to numerical information determined from detection data and if first positive information is superior to second positive information in regard to the positive information, the point 250 may move from the center 260. That is, the point 250 may move from the center 260 by a first distance d1 according to a first difference value between the positive information and the negative information, and thereafter may move from the center 260 by a second distance d2 according to a second difference value between the first positive information and the second positive information. Referring to FIG. 8F, the display regions 810, 820, and 830 may be displayed by being generated in different sizes according to the movement of the point 250. Therefore, a competitive or balanced state can be intuitively compared among the three types of information.

Referring to FIGS. 9A to 9F, if there are three pieces of numerical information to be displayed in the information display screen 200 according to various embodiments, three display regions 910, 920, and 930 may be included. The first display region 910 may display first positive information. The second display region 920 may display second positive information. The third display region 930 may display negative information. The point 250 may move from the center 260 in accordance with a first difference value which is a numerical difference between the positive information and the negative information. Further, the point 250 may move from the center 260 in accordance with a second difference value which is a numerical difference between the first positive information and the second positive information. That is, the point 250 may move from the center 260 by considering both of the first difference value and the second difference value.

Referring to FIG. 9A, in an initial state, the point 250 may be located in the center 260 of the information display screen 200, and as shown in FIG. 9B, the display regions 910, 920, and 930 may be displayed to have the same central angles θ1, θ2, and θ3 and have the same size. That is, if the number of the display regions 910, 920, and 930 is 3, the display regions 910, 920, and 930 may respectively have central angles θ1, θ2, and θ3 of 120°. When the display regions 910, 920, and 930 having the same central angle divide the information display screen 200, a size of the central angle may vary depending on the number of display regions. For example, if the number of display regions is n, the size of the central angle may be 360/n degrees (°).

Referring to FIG. 9C, if positive information is superior to negative information in regard to numerical information determined from detection data and if second positive information is superior to first positive information in regard to the positive information, the point 250 may move from the center 260. That is, the point 250 may move from the center 260 by a first distance d1 according to a first difference value between the positive information and the negative information, and thereafter may move from the center 260 by a second distance d2 according to a second difference value between the first positive information and the second positive information. Next, as shown in FIG. 9D, the display regions 910, 920, and 930 may be displayed by being generated in different sizes according to the movement of the point 250. In this case, the display regions 910, 920, and 930 may be displayed while maintaining the same central angles θ1, θ2, and θ3.

Referring to FIG. 9E, if negative information is superior to positive information in regard to numerical information determined from detection data and if first positive information is superior to second positive information in regard to the positive information, the point 250 may move from the center 260. That is, the point 250 may move from the center 260 by a first distance d1 according to a first difference value between the positive information and the negative information, and thereafter may move from the center 260 by a second distance d2 according to a second difference value between the first positive information and the second positive information. Referring to FIG. 9F, the display regions 910, 920, and 930 may be displayed by being generated in different sizes according to the movement of the point 250. In this case, the display regions 910, 920, and 930 may be displayed while maintaining the same central angles θ1, θ2, and θ3.

Next, the controller 180 may detect an operational input in operation 517. The controller 180 may detect a rotation input or a touch input in operation 517. The rotation input may include a shake operation of shaking the electronic device 100, an operation of rotating the electronic device 100, an operation of tilting the electronic device 100, or the like. The touch input may include an operation of tapping the information display screen 200 or the like. Next, the controller 180 may change the display regions 210 and 220 according to the operational input in operation 519.

Figure 10A:
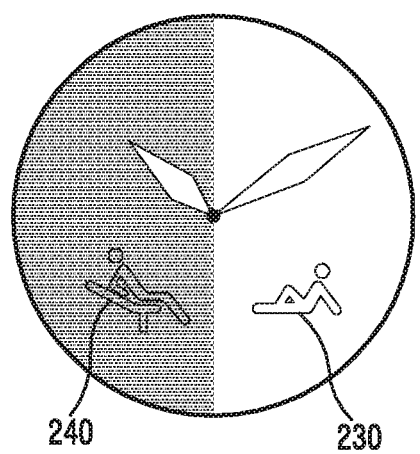
Figure 10B:
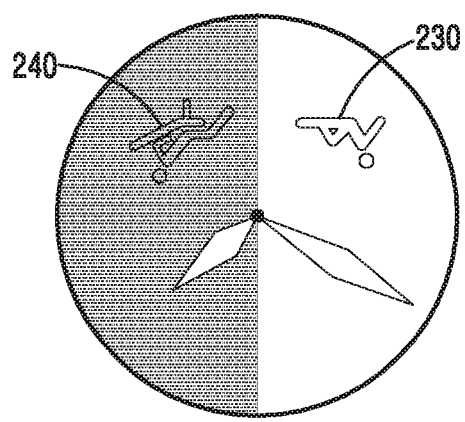

Referring to FIG. 10A, an operation of shaking objects 230 and 240 may be performed upon inputting the operation of shaking the electronic device. Further, as shown in FIB. 10B, upon inputting the operation of rotating the electronic device 100, the objects 230 and 240 may be displayed by changing a position and direction thereof or the information display screen 220 may be displayed by changing a direction thereof.

Further, the controller 180 may change the display regions 210 and 220 according to the touch input in operation 519. Referring to FIG. 11A, if the display regions 210 and 220 are displayed in a shape of a circular water drop, they may be displayed with an animation effect in which the water drop changes in response to the touch input of the display regions 210 and 220. That is, when the display regions 210 and 220 are tapped, a reaction depending on a priority of matter may be provided.

Referring to FIG. 11B, upon inputting the operation of tilting the electronic device 100, the display regions 210 and 220 may be displayed by changing a position thereof. If a size of the first display region 210 is greater than a size of the second display region 220, upon inputting the operation of tilting the electronic device 100, the first display region 210 having a relatively greater size may move in a tilting direction. That is, a weight can be displayed depending on a size. A user experience can be extended by providing such an amusing experience.

Next, if the operational input is not detected in operation 517, the controller 180 returns to FIG. 3.

Characteristics, structures, effects, and so on described in the above embodiments are included in at least one of the embodiments of the present disclosure, but are not limited to only one embodiment. Furthermore, it is apparent that the features, the structures, the effects, and so on described in the respective embodiments can be combined or modified with other embodiments by those ordinarily skilled in the art. Therefore, it is understood that such combination and modification is included within the scope of the present disclosure.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An operating method comprising:
   collecting detection data;
   determining numerical information comprising first information and second information by analyzing the detection data;
   determining, according to a difference value between a value of the first information and a value of the second information, a position of an indicator for dividing a screen into a first display region and a second display region, wherein a size of the first display region corresponds to the value of the first information and a size of the second display region corresponds to the value of the second information, wherein the screen is divided into the first display region and the second display region by the indicator; and
   displaying the screen comprising the first display region and the second display region,
   wherein the screen includes:
      a first region in which the indicator is capable of moving, and
      a second region in which movement of the indicator is restricted.

2. The operating method of claim 1, wherein the first display region and the second display region are displayed in any one of a shape of a semi-circle, a shape of a circle, a shape of a block, and a shape of a line.

3. The operating method of claim 1, wherein the determining of the numerical information comprises determining the numerical information based on the detection data within a predefined time from receiving a request for displaying the screen.

4. The operating method of claim 1, wherein the detection data comprises at least one of data detected through measurement, data detected through communication, and data detected through a user input.

5. The operating method of claim 1, wherein the numerical information comprises time information.

6. The operating method of claim 1, wherein the first information comprises an active time, and the second information comprises an inactivity time.

7. The operating method of claim 1, further comprising:
   changing the screen,
   wherein the first display region and the second display region comprise an object, and wherein changing the screen comprises changing the object.

8. The operating method of claim 1, wherein the first display region and the second display region vary in size according to a movement distance of the indicator.

9. The operating method of claim 1, wherein the displaying of the screen comprises displaying the screen so as to overlap with content which has been displayed on a display.

10. An electronic device comprising:
a display unit; and
a controller operatively coupled to the display unit,
wherein the controller is configured to:
collect detection data,
determine numerical information comprising first information and second information by analyzing the detection data,
determine, according to a difference value between a value of the first information and a value of the second information, a position of an indicator for dividing a screen into a first display region and a second display region, wherein a size of the first display region corresponds to the value of the first information and a size of the second display region corresponds to the value of the second information, wherein the screen is divided into the first display region and the second display region by the indicator, and
display the screen comprising the first display region and the second display region,
wherein the screen includes:
a first region in which the indicator is capable of moving, and
a second region in which movement of the indicator is restricted.

11. The electronic device of claim 10, wherein the first information comprises an active time, and the second information comprises an inactivity time.

12. The electronic device of claim 10, wherein the numerical information is determined based on the detection data within a predefined time from receiving a request for displaying the screen.

13. The electronic device of claim 10, wherein the detection data comprises at least one of data detected through measurement, data detected through communication, and data detected through a user input.

14. The electronic device of claim 10, wherein the numerical information comprises time information.

* * * * *